United States Patent [19]

Uematsu et al.

[11] Patent Number: 4,877,602

[45] Date of Patent: Oct. 31, 1989

[54] TRANSPARENT DENTIFRICES

[75] Inventors: Michio Uematsu, Isehara; Nobuo Suganuma, Narashino, both of Japan

[73] Assignee: Lion Corporation, Tokyo, Japan

[21] Appl. No.: 121,799

[22] Filed: * Nov. 17, 1987

Related U.S. Application Data

[63] Continuation-in-part of Ser. No. 879,606, Jun. 27, 1986, abandoned.

[30] Foreign Application Priority Data

Jun. 28, 1985 [JP] Japan .................................. 60-142709

[51] Int. Cl.⁴ .......................... A61K 7/16; A61K 7/26
[52] U.S. Cl. ...................................................... 424/49
[58] Field of Search ..................................... 424/49, 58

[56] References Cited

U.S. PATENT DOCUMENTS 3,934,000 1/1976 Barth ..................................... 424/49
4,294,894 10/1981 Vellucci ................................ 424/49

Primary Examiner—Delbert R. Phillips
Assistant Examiner—F. T Moezie
Attorney, Agent, or Firm—Birch, Stewart, Kolasch & Birch

[57] ABSTRACT

A transparent dentifrice is provided wherein a cellulose derivative, typically CMC-Na, having a viscosity of 5 to 20 centipoises measured as 1% aqueous solution at 25° C. is blended as a binding agent.

19 Claims, No Drawings

TRANSPARENT DENTIFRICES

This application is a continuation-in-part of application Ser. No. 879,606 filed on June 27, 1986, and now abandoned.

BACKGROUND OF THE INVENTION

This invention relates to transparent dentifrices having high transparency and appropriate fluidity.

Transparent dentifrices are becoming more popular because of their transparent appearance. Dentifrices have a higher degree of transparency are desirable to meet the current satisfaction of consumers. A variety of proposals have heretofore been made to increase the transparency of transparent dentifrices. Most of the past transparency improvements are based on the development of abrasives including aluminosilicate (Japanese Patent Application Kokai No. 47-39643), silica (Japanese Patent Publication No. 50-899), precipitated silica (Japanese Patent Application Kokai No. 49-80256), and silica xerogel (Japanese Patent Application Kakai No. 48-49936). In addition, it was also proposed to add laponite to the vehicle in order to increase transparency (Japanese Patent Application Kokai No. 47-11150).

As is well known in the art, usual transparent dentifrices contain sodium carboxymethylcellulose (to be abbreviated as CMC-Na, hereinafter) in the vehicle as a binding agent. We have discovered that CMC-Na's commonly used as the binder in dentifrices cause turbidity when blended in transparent dentifrices. Even though the transparency of an abrasive itself is improved by a successful abrasive development or an additive regarded as effective in transparency improvement is added, the transparency of transparent dentifrices is improved only to a limited extent as long as CMC-Na is utilized.

U.S. Pat. No. 3,934,000 discloses a transparent toothpaste containing 0.2 to 2% of sodium carboxymethylcellulose (CMC-Na) having about 0.6 to 0.8 carboxymethyl groups per anhydroglucose unit. According to this patent, CMC-Na in its particularly preferred form has an average degree of polymerization in the neighborhood of 500, corresponding to a molecular weight in the neighborhood of 100,000. For instance one may use a material whose viscosity (of a 2% aqueous solution thereof at 25° C.) is less than 3,000 centipoises, preferably below 1,000, e.g. about 300 to 600 centipoises, such as Hercules CMC-7MXF which has about 0.7 sodium carboxymethyl groups per anhydroglucose unit. It should be noted that a viscosity of 300 centipoises measured as 2 % aqueous solution of CMC-Na at 25° C. corresponds to a viscosity of about 43 centipoises measured as 1% aqueous solution of CMC-Na at 25° C.

U.S. Pat. No. 4,294,894 discloses a transparent toothpaste containing sodium chloride in amounts ranging from 0.5 to 20% by weight of the toothpaste.

There is a need for further increasing the transparency of transparent dentifrices by eliminating the turbidity of transparent dentifrices associated with the use of CMC-Na as a binding agent.

SUMMARY OF THE INVENTION

It is an object of the present invention to provide a highly transparent dentifrice free from turbidity comprising a cellulose derivative binding agent.

Making extensive investigations on binding agents which do not render transparent dentifrices turbid we have found that among cellulose derivatives such as CMC-Na's, those cellulose derivatives having a viscosity of 5 to 20 centipoises measured as 1% aqueous solution at 25° C. can unexpectedly be blended in transparent dentifrices to accomplish increased transparency rather than inviting turbidity.

Various forms of CMC-Na were used as the binding agent in prior art dentifrices. For example, Japanese Patent Application Kokai No. 50-12242 proposes to use a certain form of CMC-Na having a viscosity of 28 to 32 centipoises measured as 1% aqueous solution at 25° C. as the binding agent in conventional opaque dentifrices. The CMC-Na's used in the conventional dentifrices have a viscosity of the order of 30 to 200 centipoises measured as 1% aqueous solution at 25° C. When these CMC-Na's are blended in transparent dentifrices in usual quantities, the resulting dentifrices become turbid. It is difficult to impart a degree of transparency of 4 cm or more as measured by the transparency measurement procedure for transparent dentifrices as will be defined later. On the contrary, the use of cellulose derivatives having a viscosity of 5 to 20 centipoises measured as 1% aqueous solution at 25° C. ensures that turbidity-free transparent dentifrices having a degree of transparency of 4 cm or more be readily produced. This is first discovered by the present inventors.

Therefore, the present invention provides a transparent dentifrice wherein a cellulose derivative having a viscosity of 5 to 20 centipoises measured as 1% aqueous solution at 25° C. is blended as a binding agent.

Since a cellulose derivative having a viscosity of 5 to 20 centipoises measured as 1% aqueous solution at 25° C. is blended as a binding agent, the transparent dentifrices of the present invention are turbidity-free and thus exhibit a high degree of transparency.

There and other objects, features and advantages of the present invention will be more apparent from the following description.

DETAILED DESCRIPTION OF THE INVENTION

The transparent dentifrices (toothpastes) of the present invention are generally prepared by combining together an abrasive with a transparent vehicle having substantially the same refractive index as the abrasive. According to the present invention, a cellulose derivative having a viscosity of 5 to 20 centipoises measured as 1% aqueous solution at 25° C. is blended as a binding agent in the transparent vehicle.

1% aqueous solution of the cellulose derivatives has a viscosity ranging from 5 to 20 centipoises, inclusive, as mentioned above. Within this viscosity range, turbidity-free, high transparent dentifrices are manufactured with the use of a cellulose derivative binding agent. Cellulose derivatives having a viscosity of less than 5 centipoises will invite turbidity in transparent dentifrices because they must be blended in large amounts to provide the necessary dentifrice viscosity or combined with another binding agent as a main binding agent. Cellulose derivatives having a viscosity of more than 20 centipoises cause turbidity as such. The method for measuring the viscosity of 1% aqueous solution of cellulose derivative will be described later.

Preferred among the cellulose derivatives having a viscosity of 5 to 20 centipoises measured as 1% aqueous solution are those having an average degree of substitution of at least 0.9. The upper limit of the average degree of substitution is not particularly limited, although it may be 1.5. Turbidity sometimes occurs to lower transparency if the average degree of substitution is 0.8 or less.

The cellulose derivatives include carboxymethyl hydroxyethyl cellulose and sulfated cellulose although alkali metal salts of carboxyalkyl celluloses, especially alkali metal salts of carboxymethyl cellulose such as CMC-Na, are preferably used.

The amount of the cellulose derivatives blended is not particularly limited. Since the cellulose derivatives have a viscosity as low as 5 to 20 centipoises measured as 1% aqueous solution, they are preferably blended in amounts of 1 to 4% by weight, more preferably 1 to 2% by weight, of the total weight of the dentifrice composition so that the resulting dentifrices have the desired viscosity of 500 to 900 poises at 25° C.

In the practice of the present invention, other binding agents may be optionally used in addition to the present cellulose derivatives. Examples of the additional binding agents are carrageenan, gums, polyvinyl alcohol, carboxyvinyl polymers, polyvinyl pyrolidone, and the like. The amount of the additional binding agents blended preferably ranges from 0 to 0.5% by weight of the total dentifrice composition. Even cellulose derivatives having a viscosity of at least 30 centipoises measured as 1% aqueous solution may also be added in limited amounts as long as the transparency of the resulting dentifrices is not adversely affected.

In the transparent dentifrices of the present invention, the abrasive and the ingredients with which the transparent vehicle is made up except the binding agent may be any of such materials commonly used in the preparation of transparent dentifrices.

Examples of the abrasives used herein include well-known synthesized amorphous silicas and synthesized amorphous silicates having 0.05 to 20% by weight of Al, Zr or other metals attached to silica, such as aluminosilicate and zirconosilicate. No particular limit is imposed on the abrasive in the practice of the present invention, although a silica and/or a silicate having a refractive index of 1.43 to 1.46 is used as a main abrasive. The blending amount of the abrasive may preferably be in the range of from 5% to 50% by weight of the composition.

In preparing the transparent vehicles, various ingredients may be blended in addition to the above-mentioned binding agent and water, for example, humectants such as polyethylene glycol, sorbitol, glycerin, propylene glycol, etc.; surface active agents such as sodium lauryl sulfate, sodium dedecylbenzen-sulfonate, sodium hydrogenated coconut fatty acid monogylceride monosulfate, sodium lauryl sulfoacetate, sodium N-lauroylsarcosinate, N-acylglutamates, lauroyl diethanolamide, sucrose fatty acid esters, etc.; flavoring agents, for example, essential oils such as peppermint oil, spearmint oil, etc. and flavors such as l-menthol, carbone, eugenol, anetol, etc.; sweeteners such as sodium saccharin, stevioside, neohesperidyl dihydrochalcone, glycyrrhizin, perillartine, p-methoxycinnamic aldehyde, somatine, etc.; preservatives; and effective ingredients such as lysozyme chloride, dextranase, bacteriolytic enzymes, mutanase, chlorhexidine and salts thereof, sorbic acid, alexidine, hinokitiol, cetyl pyridinium chloride, alkyl glycines, alkyl diaminoethyl glycine salts, allantoin, α-aminocaproic acid, tranexamic acid, azulene, vitamin E, sodium monofluorophosphate, sodium fluoride, stannous fluoride, water-soluble primary and secondary phosphoric acid salts, quanternary ammonium compounds, etc. The other additives such as Laponite ®, maltodextrin, etc. may also be added.

It should be noted that sodium chloride will deteriorate the transparency of the transparent dentifrice using a cellulose derivative having a viscosity of 5 to 20 centipoises measured as 1% aqueous solution.

The content of the humectant may be in the range of 1 to 70% by weight, preferably 10 to 60% by weight of the composition. The content of the surface active agent may be in the range of 0.1 to 10% by weight, preferably 0.2 to 5% by weight of the composition. The content of the flavor may be in the range of 0.1 to 5% by weight, preferably 0.3 to 2% by weight of the composition. The content of the sweetener may be in the range of 0.001 to 5% by weight, preferably 0.005 to 2% by weight of the composition.

The transparent dentifrices of the present invention may be prepared by combining together the abrasive and the transparent vehicle both having a substantially equal refractive index. The preferred refractive index ranges from about 1.43 to 1.46. Those dentifrices having a reduced amount of humectant blended and hence, a low refractive index are desirable with respect to taste. The pH of the composition may preferably be in the range of 4 to 8.

Examples of the present invention are given below by way of illustration and not by way of limitation. All percents are by weight.

EXAMPLE 1

Transparent dentifrices of the following formulation were prepared and measured for transparency. The results are shown in Table 1.

| Transparent dentifrice formulation | % by weight |
| --- | --- |
| Fumed silica | 2.0 |
| Aluminosilicate | 20 |
| Polyethylene glycol #400 | 5 |
| 70% sorbitol solution | 38.0 |
| 95% glycerin solution | 19.0 |
| CMC-Na | reported in Table 1 |
| Sodium lauryl sulfate | 1.0 |
| N—lauroyl sarcosinate | 0.2 |
| Sodium saccharin | 0.1 |
| Flavor | 1.0 |
| Purified water | balance |
|  | 100.0% |
| Refractive index | 1.440 |
| Dentifrice viscosity | 750 poises at 25° C. |

TABLE 1

|  | Invention | | Comparison | |
|  | Sample 1 | Sample 2 | Sample 3 | Sample 4 |
| --- | --- | --- | --- | --- |
| CMC-Na |  |  |  |  |
| Viscosity @ 1% solution | 8 centipoise | 15 centipoise | 55 centipoise | 105 centipoise |
| Average degree of esterification | 0.9 | 1.1 | 0.6 | 0.9 |
| Amount blended | 1.5% | 1.3% | 1.1% | 1.0% |
| Properties |  |  |  |  |
| Transparency | E | E | F | F |
| Stringiness | G | G | G | G |
| Shape retention | G | G | G | G |

The method for measuring the viscosity of 1% aqueous solution of CMC-Na and the procedures for evaluating transparency, stringiness, and shape retention are described below.

Viscosity measurement of 1% aqueous solution

A specimen of CMC-Na is dissolved in water to a concentration of 1% by weight. The 1% solution is aged for 5 hours to allow the CMC-Na to be fully swollen before it is measured for viscosity by means of a BL rotary viscometer at 25° C.

Transparency measurement

A cylindrical container having a transparent bottom where two making lines are drawn at a spacing of 1 mm is filled with a transparent dentifrice sample. With light directed from below to the bottom of the container, visual observation is made from the top of the dentifrice sample to determine the maximum height of the dentifrice sample at which the two marking lines are discernible from each other.

| Judgment criterion | |
|---|---|
| E: excellent transparency | $\geq 5.0$ cm |
| G: good transparency | 4–5 cm |
| F: clear appearance, but less transparency | 2–4 cm |
| B: bad transparency | $\leq 2$ cm |

Stringiness

The stringiness of a dentifrice sample is evaluated in accordance with the following criterion.
G: good
F: rather poor though acceptable in actual use
B: bad Shape retention The shape retention of a dentifrice sample is evaluated in accordance with the following criterion.
G: good
F: grow somewhat round or dull
B: grow round or dull

EXAMPLE 2

| Example 2 | % by weight |
|---|---|
| Zirconosilicate | 18 |
| Fumed silica | 2.0 |
| 70% sorbitol | 60.0 |
| Polyethylene glycol #400 | 4.0 |
| CMC-Na | 1.5 |
| (Viscosity @ 1% aqueous solution | 8 centipoise) |
| (average degree of etherification | 1.0) |
| Sodium lauryl sulfate | 1.5 |
| Lauroyl diethanol amide | 0.5 |
| Sodium saccharin | 0.1 |
| Flavor | 1.0 |
| Chlorhexidine | 0.05 |
| Purified water | balance |
| | 100.0% |
| Refractive index . . . 1.452, | Viscosity . . . 690 poises |

EXAMPLE 3

| Example 3 | % by weight |
|---|---|
| Precipitated silica | 20 |
| Fumed silica | 2.5 |
| 96% Glycerin | 17 |
| 70% sorbitol | 40 |
| CMC-Na | 1.3 |
| (Viscosity @ 1% aqueous solution | 15 centipoise) |
| (average degree of etherification | 1.2) |
| α-olefin sulfonate | 1.5 |

-continued

| Example 3 | % by weight |
|---|---|
| Lauroyl diethanol amide | 0.3 |
| Sodium saccharin | 0.1 |
| Flavor | 1.0 |
| Tranexamic acid | 0.05 |
| Purified water | balance |
| | 100.0% |
| Refractive index . . . 1.433, | Viscosity . . . 780 poises |

EXAMPLE 4

| Example 4 | % by weight |
|---|---|
| Aluminosilicate | 15 |
| Fumed silica | 2.5 |
| 96% Glycerin | 10 |
| 70% sorbitol | 45 |
| Polyethylene glycol #400 | 5.0 |
| CMC-Na | 1.2 |
| (Viscosity @ 1% aqueous solution | 22 centipoise) |
| (average degree of etherification | 1.5) |
| Sucrose fatty acid ester | 2.0 |
| Lauroyl diethanol amide | 0.5 |
| Sodium saccharin | 0.1 |
| Flavor | 1.0 |
| Dextranase | 0.2 |
| Purified water | balance |
| | 100.0% |
| Refractive index . . . 1.432, | Viscosity . . . 820 poises |

EXAMPLE 5

| Example 5 | % by weight |
|---|---|
| Zirconosilicate | 20 |
| Fumed silica | 2.0 |
| 96% Glycerin | 15 |
| 70% sorbitol | 40 |
| Polyethylene glycol #400 | 5.0 |
| CMC-Na | 2.2 |
| (Viscosity @ 1% aqueous solution | 5 centipoise) |
| (average degree of etherification | 1.0) |
| Sodium lauryl sulfate | 1.5 |
| Lauroyl diethanol amide | 0.3 |
| Sodium saccharin | 0.1 |
| Flavor | 1.0 |
| Sodium monofluorophosphate | 0.76 |
| Purified water | balance |
| | 100.0% |
| Refractive index . . . 1.441, | Viscosity . . . 730 poises |

EXAMPLE 6

| Example 6 | % by weight |
|---|---|
| Precipitated silica | 13 |
| Fumed silica | 2.5 |
| 70% sorbitol | 60 |
| Polyethylene glycol #400 | 5.0 |
| CMC-Na | 1.5 |
| (Viscosity @ 1% aqueous solution | 25 centipoise) |
| (average degree of etherification | 0.9) |
| α-olefin sulfonate | 1.5 |
| Lauroyl diethanol amide | 0.5 |
| Sodium saccharin | 0.1 |
| Flavor | 1.0 |
| Sodium monofluorophosphate | 0.76 |
| Purified water | balance |
| | 100.0% |
| Refractive index . . . 1.436, | Viscosity . . . 790 poises |

All the transparent dentifrices prepared in Examples 2 through 6 had excellent transparent as rated to be more than 5 cm according to the foregoing transparency measurement procedure.

It should be noted that the transparency of a dentifrice prepared by the same formulation as in Example 2 except that 16% of NaCl is blended instead of the same amount (16%) of 70% sorbitol was about 2 cm.

What is claimed is;

1. A transparent dentifrice composition comprising:
   5 to 50% by weight of an abrasive having a refractive index of from 1.43 to 1.46; and
   a transparent vehicle having substantially the same refractive index as said abrasive and comprising,
   1 to 4% by weight of sodium carboxymethyl cellulose,
   1 to 70% by weight of a humectant,
   0.1 to 10% by weight of a surface active agent,
   0.1 to 5% by weight of a flavor, and
   0.001 to 5% by weight of a sweetener,
   said sodium carboxymethyl cellulose having a viscosity of 5 to 20 centipoises measured as 1% aqueous solution at 25° C. and having an average degree of substitution of from 0.9 to 1.5.

2. A dentifrice composition according to claim 1 wherein said abrasive is a silica, a silicate or mixture thereof having a refractive index of 1.43 to 1.46.

3. A dentifrice composition according to claim 1, wherein the composition has a viscosity of 500 to 900 poises at 25° C.

4. A dentifrice composition according to claim 1, wherein said sodium carboxymethyl cellulose has a viscosity of 8 to 15 centipoises measured as 1% aqueous solution at 25° C. as a binding agent.

5. A dentifrice composition according to claim 4, wherein said sodium carboxymethyl cellulose has an average degree of substitution of 0.9 to 1.1.

6. A dentifrice composition according to claim 5, wherein said sodium carboxymethyl cellulose is blended in amounts of 1 to 4% by weight of the total weight of the composition.

7. A transparent dentifrice composition consisting essentially of: 5 to 50% by weight of an abrasive having a refractive index of from 1.43 to 1.46; and
   a transparent vehicle having substantially the same refractive index as said abrasive and comprising,
   1 to 4% by weight of sodium carboxymethyl cellulose,
   1 to 70% by weight of a humectant,
   0.1 to 10% by weight of a surface active agent,
   0.1 to 5% by weight of a flavor, and
   0.001 to 5% by weight of a sweetener,
   said sodium carboxymethyl cellulose having a viscosity of 5 to 20 centipoises measured as 1% aqueous solution at 25° C., having an average degree of substitution of from 0.9 to 1.5.

8. A dentifrice composition according to claim 1, which is exclusive of sodium chloride.

9. A dentifrice composition according to claim 1, which has a degree of transparency of about 4 cm.

10. A dentifrice composition according to claim 6, which has a degree of transparency of about 4 cm.

11. A dentifrice composition according to claim 1, wherein said sodium carboxymethyl cellulose is blended in amounts of 1 to 2% by weight of the total weight of the composition.

12. A dentifrice composition according to claim 5, wherein said cellulose is blended in amounts of 1 to 2% by weight of the total weight of the composition.

13. A dentifrice composition according to claim 1, which further comprises an additional binding agent selected from the group consisting of carrageenan, gums, polyvinyl alcohol, carboxyvinyl polymers, and polyvinyl pyrolidone.

14. A dentifrice composition according to claim 7, which further consists essentially of an additional binding agent selected from the group consisting of carrageenan, gums, polyvinyl alcohol, carboxyvinyl polymers, and polyvinyl pyrolidone.

15. A dentifrice composition according to claim 1, which further comprises preservatives.

16. A dentifrice composition according to claim 7, which further consists essentially of preservatives.

17. A dentifrice composition according to claim 1, wherein said sodium carboxymethyl cellulose has an average degree of substitution of 0.9 to 1.1.

18. A dentifrice composition according to claim 17, which has a degree of transparency of about 4 cm.

19. A dentifrice composition according to claim 6, wherein said abrasive is a silica, a silicate or mixture thereof having a refractive index of 1.43 to 1.46.

* * * * *